United States Patent [19]

Lafon

[11] 4,124,706
[45] Nov. 7, 1978

[54] ESTERS OF BIS-(HYDROXYALKYLTHIO)-ALKANES

[75] Inventor: Louis Lafon, Paris, France

[73] Assignee: Societe Anonyme dite: Laboratoire L. Lafon, France

[21] Appl. No.: 782,918

[22] Filed: Mar. 30, 1977

[30] Foreign Application Priority Data

Apr. 2, 1976 [GB] United Kingdom ............... 13488/76

[51] Int. Cl.² ........................ A61K 31/60; C07C 69/90
[52] U.S. Cl. ........................................ 424/230; 560/66
[58] Field of Search ........................... 560/66; 424/230

[56] References Cited

U.S. PATENT DOCUMENTS

| 1,063,099 | 5/1913 | Wolffenstein | 560/66 |
| 3,769,436 | 10/1973 | Lafon | 424/311 |

FOREIGN PATENT DOCUMENTS 824,716  5/1975  Belgium.

Primary Examiner—Jane S. Myers
Attorney, Agent, or Firm—Jacobs & Jacobs

[57] ABSTRACT

Esters of acetylsalicylic acid with polyols of the formula:

$$HO - A - S - (CH_2)_n - S - A - OH \qquad (I)$$

in which n is an integer of from 5 to 15 and each A group represents a $C_2$-$C_6$ linear or branched hydrocarbyl group which can contain an —OH group are particularly useful as hypolipidaemic, hypocholesterolaemic, anti-blood clotting and anti-atherosclerosis agents.

18 Claims, No Drawings

ESTERS OF BIS-(HYDROXYALKYLTHIO)-ALKANES

The present invention relates to certain esters of bis-(hydroxyalkylthio)-alkanes and to their therapeutic application, especially in the treatment of cardiovascular diseases.

It is known that certain bis-(hydroxyalkylthio)-alkanes are useful as hypolipidaemic and hypocholesterolaemic agents (see, for example, British Pat. Specification No. 1,307,227, French Pat. Specification No. 2,146,138 and British Pat. application No. 41381/74).

It has now been discovered that particular esters of the said bis-(hydroxyalkylthio)-alkanes possess valuable therapeutic properties, especially in the cardio-vascular field. These compounds, which are novel per se, are esters of acetylsalicylic acid, as hereinafter defined, with the polyols of the formula

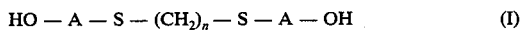

in which $n$ is an integer from 5 to 15 and each A group represents a $C_2$-$C_6$ linear or branched hydrocarbyl group which can contain an OH group.

The term "esters of acetylsalicyclic acid" as used herein includes both mono-acetylsalicylates of the polyol (I) which may be obtained by suitably protecting one —OH of the polyol (I), and the diacetylsalicylates of formula

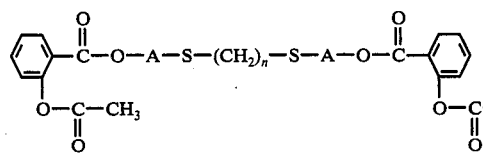

in which A and $n$ are as defined above.

Examples of suitable groups for A are the —CH$_2$CH$_2$—, —CH(CH$_3$)CH$_2$—, —CH$_2$CH(CH$_3$)—, —C(CH$_3$)$_2$CH$_2$—, —CH$_2$C(CH$_3$)$_2$—, —C(CH$_3$)$_2$C(CH$_3$)$_2$—, —CH$_2$CHOHCH$_2$—, —CH(CH$_2$OH)CH$_2$CH$_2$—, —CH$_2$CH$_2$CH$_2$— and —CH$_2$CH(CH$_3$)CH$_2$— groups.

The acetylsalicylates of the invention can be prepared by methods known per se. The preferred method for the synthesis of the esters consists of reacting acetylsalicyloyl chloride with a polyol of the formula I in the presence of a base, especially an amine, under stoichiometric conditions, or in the presence of an excess of acetylsalicyloyl chloride.

Particularly preferred bis-(hydroxyalkylthio)-alkanes of formula I which can be used to obtain the esters of the invention are those listed in Table I.

Table I

| | | (CH$_2$)$_n$[—S—A—OH]$_2$ | | |
|---|---|---|---|---|
| Code | Number | n | A | Melting Point |
| LL | 1,558 | 10 | —CH$_2$CH$_2$— | 70–71° C |
| LL | 1,089 | 5 | —CH$_2$CH$_2$— | 85° C |
| — | — | 12 | —CH$_2$CH$_2$— | 78° C |
| CRL | 40,055 | 10 | —C(CH$_3$)$_2$CH$_2$— | <50° C |
| CRL | 40,077 | 8 | —CH$_2$CH$_2$— | 59° C |

Table I-continued

| | | (CH$_2$)$_n$[—S—A—OH]$_2$ | | |
|---|---|---|---|---|
| Code | Number | n | A | Melting Point |
| CRL | 40,085 | 6 | —CH$_2$CH$_2$— | 47° C |
| CRL | 40,116 | 9 | —CH$_2$CH$_2$— | 64° C |
| CRL | 40,120 | 7 | —CH$_2$CH$_2$— | 50° C |
| CRL | 40,122 | 10 | —CH(CH$_3$)CH$_2$— | 47–48° C |
| CRL | 40,155 | 10 | —CH$_2$CHOHCH$_2$— | 95° C |
| CRL | 40,176 | 10 | —CH(CH$_2$OH)CH$_2$CH$_2$— | 73° C |
| CRL | 40,193 | 9 | —CH(CH$_3$)CH$_2$— | 20° C |
| CRL | 40,194 | 11 | —CH$_2$CH$_2$— | 73° C |

Note: the melting points were determined on a Kofler bench (instantaneous melting point).

The most useful esters from a therapeutic point of view are the diacetylsalicylates obtained from LL 1,558, i.e. 3,14-dithia-1,16-hexadecanediol (alternative nomenclature: 1,10-bis-(2-hydroxyethylthio)-decane) and from CRL 40,122 2,15-dimethyl-3,14-dithia-1,16-hexadecanediol.

The invention also provides a therapeutic composition comprising, as active ingredient, at least one acetylsalicylate of the invention in association with a physiologically acceptable excipient. The compound of the invention acts as a hypolipidaemic and hypocholesterolaemic agent.

The invention is illustrated by the following Examples.

EXAMPLE 1

1,16-Di-(O-acetylsalicyloyloxy)-3,14-dithiahexadecane alternative nomenclature: 1,16-(3,14-dithiahexadecyl)di-(O-acetylsalicylate)

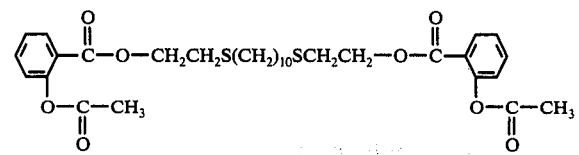

A solution of 8.5 g (0.042 mol) of acetylsalicyloyl chloride in 50 ml of benzene is run over the course of 1 hour into a suspension of 5.9 g (0.020 mol) of 3,14-dithia-1,16-hexadecanediol (LL 1,558) and of 4.25 g (0.042 mol) of triethylamine in 50 ml. of benzene. The reaction mixture is stirred for 3 hours at ambient temperature (15°–25° C.) and is diluted with diethyl ether. After washing the organic phase with water and with a potassium carbonate solution, drying it and evaporating the solvent, 14 g of a slightly pink limpid oil are obtained. 8.7 g of this oil are purified by passing it over a silica column and then by washing with a 50:50 v/v mixture of cyclohexane and diisopropyl ether, to give 3.1 g of a white water-insoluble powder.

Instantaneous melting point (Kofler) < 40° C. Yield = 39.5%

EXAMPLE 2

1,16-Di-(O-acetylsalicyloyloxy)-2,15-dimethyl-3,14-dithia-hexadecane alternative nomenclature: 1,16-(2,15-dimethyl-3,14-dithiahexadecyl) di-(O-acetylsalicylate)

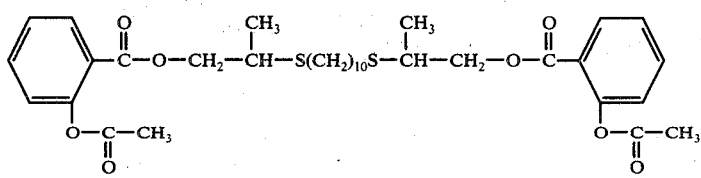

On following the procedure indicated in Example 1 but replacing the 3,14-dithia-1,16-hexadecanediol by 2,15-dimethyl-3,14-dithia-1,16-hexadecanediol, 1,16-di-(O-acetylsalicyloyloxy)-2,15-dimethyl-3,14-dithia-hexadecane is obtained.

Pharmacological tests on animals and man show that the esters of the invention, especially the products of Examples 1 and 2, reduce the lipid and cholesterol levels in the blood. Additionally, they exhibit anti-blood clotting and anti-atherosclerosis properties.

Preferably, the esters of the invention are administered orally as a therapeutic composition. The preferred dosage when treating or preventing cardio-vascular diseases is from 100 mg to 2000 mg of active ingredient per day for at least one week.

The product of Example 1 has been successfully used in man as an anti-blood clotting and anti-atherosclerosis agent when 2 to 4 gelules or capsules (each containing 500 mg of active ingredient) have been administered to the patient each day.

I claim:

1. A compound of the formula:

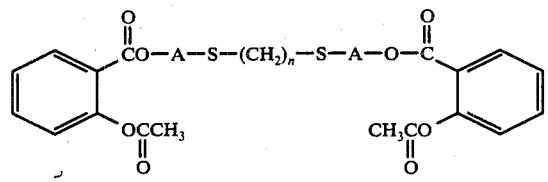

wherein
   $n$ has a value of from 5 to 15; and
   each A is alkylene of 2 to 6 carbon atoms, unsubstituted or substituted with hydroxy.

2. A compound according to claim 1, in which A is —CH$_2$CH$_2$—, —CH(CH$_3$)CH$_2$—, —CH$_2$CH(CH$_3$)—, —C(CH$_3$)$_2$CH$_2$—, —CH$_2$C(CH$_3$)$_2$—, —C(CH$_3$)$_2$C(CH$_3$)$_2$—, —CH$_2$CHOHCH$_2$—, —CH(CH$_2$OH)CH$_2$CH$_2$—, —CH$_2$CH$_2$CH$_2$— or —CH$_2$CH(CH$_3$)CH$_2$—.

3. A compound according to claim 2 wherein A is —CH$_2$CH$_2$—.

4. A compound according to claim 2 in which A is —CH$_2$CH$_2$— and $n$ is an integer of from 5 to 12.

5. A compound according to claim 2 wherein A is —CH(CH$_3$)CH$_2$—.

6. The compound according to claim 5 wherein $n$ is 9.

7. A compound according to claim 2 wherein A is —CH$_2$CHOHCH$_2$—.

8. The compound according to claim 7 wherein $n$ is 10.

9. A compound according to claim 2 wherein A is —CH(CH$_2$OH)CH$_2$CH$_2$—.

10. The compound according to claim 9 wherein $n$ is 10.

11. A compound according to claim 2 wherein A is —C(CH$_3$)$_2$CH$_2$—.

12. The compound according to claim 11 wherein $n$ is 10.

13. 1,16-Di-(O-acetylsalicyloyloxy)-3,14-dithia-hexadecane.

14. 1,16-Di-(O-acetylsalicyloyloxy)-2,15-dimethyl-3,14-dithia-hexadecane.

15. A pharmaceutical composition comprising an amount of a compound according to claim 1 sufficient to effect a hypolipidemic and hypocholesterolemic response in a patient, said compound being in combination with a pharmaceutically acceptable carrier.

16. A composition according to claim 15 wherein said composition contains a quantity of said compound sufficient to supply upon multiple daily administration a total of from 100 mg to 2000 mg of said compound per day.

17. The method of effecting a hypolipidemic and hypocholesterolemic response in a patient which comprises administering thereto an effective amount of a compound according to claim 1.

18. A method according to claim 17, in which from 100 mg to 2000 mg of said compound is administered to the patient per day.

* * * * *